United States Patent
Huang

(12) 
(10) Patent No.: US 10,528,761 B2
(45) Date of Patent: Jan. 7, 2020

(54) DATA ANONYMIZATION IN AN IN-MEMORY DATABASE

(71) Applicant: SAP SE, Walldorf (DE)

(72) Inventor: Xinrong Huang, Shanghai (CN)

(73) Assignee: SAP SE, Walldorf (DE)

( * ) Notice: Subject to any disclaimer, the term of this patent is extended or adjusted under 35 U.S.C. 154(b) by 148 days.

(21) Appl. No.: 15/794,807

(22) Filed: Oct. 26, 2017

(65) Prior Publication Data

US 2019/0130131 A1 May 2, 2019

(51) Int. Cl.
*G06F 21/00* (2013.01)
*G06F 21/62* (2013.01)
*G06F 16/28* (2019.01)

(52) U.S. Cl.
CPC ........ *G06F 21/6254* (2013.01); *G06F 16/285* (2019.01)

(58) Field of Classification Search
CPC ........... G06F 21/6254; G06F 17/30598; G06F 19/00; G06F 16/285; H04L 2209/42
See application file for complete search history.

(56) References Cited

U.S. PATENT DOCUMENTS

| | | | | |
|---|---|---|---|---|
| 5,748,973 | A * | 5/1998 | Palmer | G06F 17/27 704/9 |
| 9,177,067 | B2 * | 11/2015 | Kawecki, III | G06Q 30/0255 |
| 9,489,538 | B2 * | 11/2016 | Vyas | G06F 21/6254 |
| 10,242,277 | B1 * | 3/2019 | Manohar | G06K 9/036 |
| 2006/0104512 | A1 * | 5/2006 | Hayashi | G06K 9/4652 382/176 |
| 2010/0042583 | A1 | 2/2010 | Gervais et al. | |
| 2011/0119661 | A1 * | 5/2011 | Agrawal | G06F 21/566 717/154 |
| 2013/0138698 | A1 | 5/2013 | Harada et al. | |
| 2014/0016761 | A1 * | 1/2014 | Werner | H04M 3/5133 379/88.11 |
| 2014/0324915 | A1 * | 10/2014 | Gkoulalas-Divanis | G06F 21/6254 707/803 |
| 2014/0325666 | A1 * | 10/2014 | Gkoulalas-Divanis | G06F 21/6254 726/26 |
| 2015/0007249 | A1 * | 1/2015 | Bezzi | G06F 21/6254 726/1 |

(Continued)

FOREIGN PATENT DOCUMENTS

WO WO 2014/006851 A1 1/2014

OTHER PUBLICATIONS

Extended European Search Report, dated Sep. 27, 2018, for European Patent Appl. No. 18184489.5, 9 pages.

(Continued)

*Primary Examiner* — Don G Zhao
(74) *Attorney, Agent, or Firm* — Sterne, Kessler, Goldstein & Fox P.L.L.C.

(57) ABSTRACT

Disclosed herein are system, method, and computer program product embodiments for data anonymization in an in-memory database. An embodiment operates by identifying a textual attribute corresponding to data of an input table. A value corresponding to the textual attribute is determined for each of the plurality of records. A plurality of groups is generated based on the determined values. At least portion of the data as sorted into the plurality of groups is provided.

18 Claims, 5 Drawing Sheets

(56) References Cited

U.S. PATENT DOCUMENTS

2016/0196453 A1* 7/2016 Yamaoka ............ G06F 21/6254
726/26
2019/0034823 A1* 1/2019 Thapliyal ................ G06F 16/35

OTHER PUBLICATIONS

Lefevre, K. et al., "Mondrian Multidimensional K-Anonymity," *Proceedings of the 22nd International Conference on Data Engineering*, 11 pages (2006).
Lefevre, K. et al., "Workload-Aware Anonymization," *Proceedings of KDD*, pp. 277-286 (Aug. 20-23, 2006).
Li, N. et al., "t-Closeness: Privacy Beyond k-Anonymity and l-Diversity," *Proceedings of the 23rd IEEE International Conference on Data Engineering*, pp. 106-115 (2007).
Machanavajjhala, A. et al., "l-Diversity: Privacy Beyond k-Anonymity," *ACM Transactions on Knowledge Discovery from* Data, vol. 1, No. 1, Article 3, 52 pages. (Mar. 2007).
Sweeney, L., "k-Anonymity: A Model for Protecting Privacy," *International Journal on Uncertainty, Fuzziness and Knowledge-based Systems*, vol. 10, No. 5, pp. 557-570 (2002).
Xu, J. et al., "Utility-Based Anonymization Using Local Recoding," *Proceedings of the 12th ACM SIGKDD International Conference on Knowledge Discovery and Data Mining*, pp. 785-790, New York, NY, USA (Aug. 20-23, 2006).

* cited by examiner

DATA ANONYMIZATION IN AN IN-MEMORY DATABASE

CROSS REFERENCE TO RELATED APPLICATIONS

This application is related to U.S. patent application Ser. No. 15/794,779, filed herewith, entitled "Bottom Up Data Anonymization In An In-Memory Database,", and U.S. patent application Ser. No. 15/794,744, filed herewith, entitled "K-Anonymity and L-Diversity Data Anonymization In An In-Memory Database,", all of which are hereby incorporated by reference in their entireties.

BACKGROUND

Data anonymization is a data privacy technique in which personal information from data of a database is protected via deletion or encryption such that individuals about whom the information relates cannot be identified. Data anonymization may be used to protect the privacy of individuals or companies about whom data has been collected while at the same time maintaining the integrity of the released data that is being shared. Current techniques being used to anonymize data typically apply to numerical data or hierarchical data and cannot be applied to other types of data, such as textual data, thus limiting the anonymization options that are available.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Provided herein are system, apparatus, device, method and/or computer program product embodiments, and/or combinations and sub-combinations thereof, for data anonymization in an in-memory database.

Figure 1:
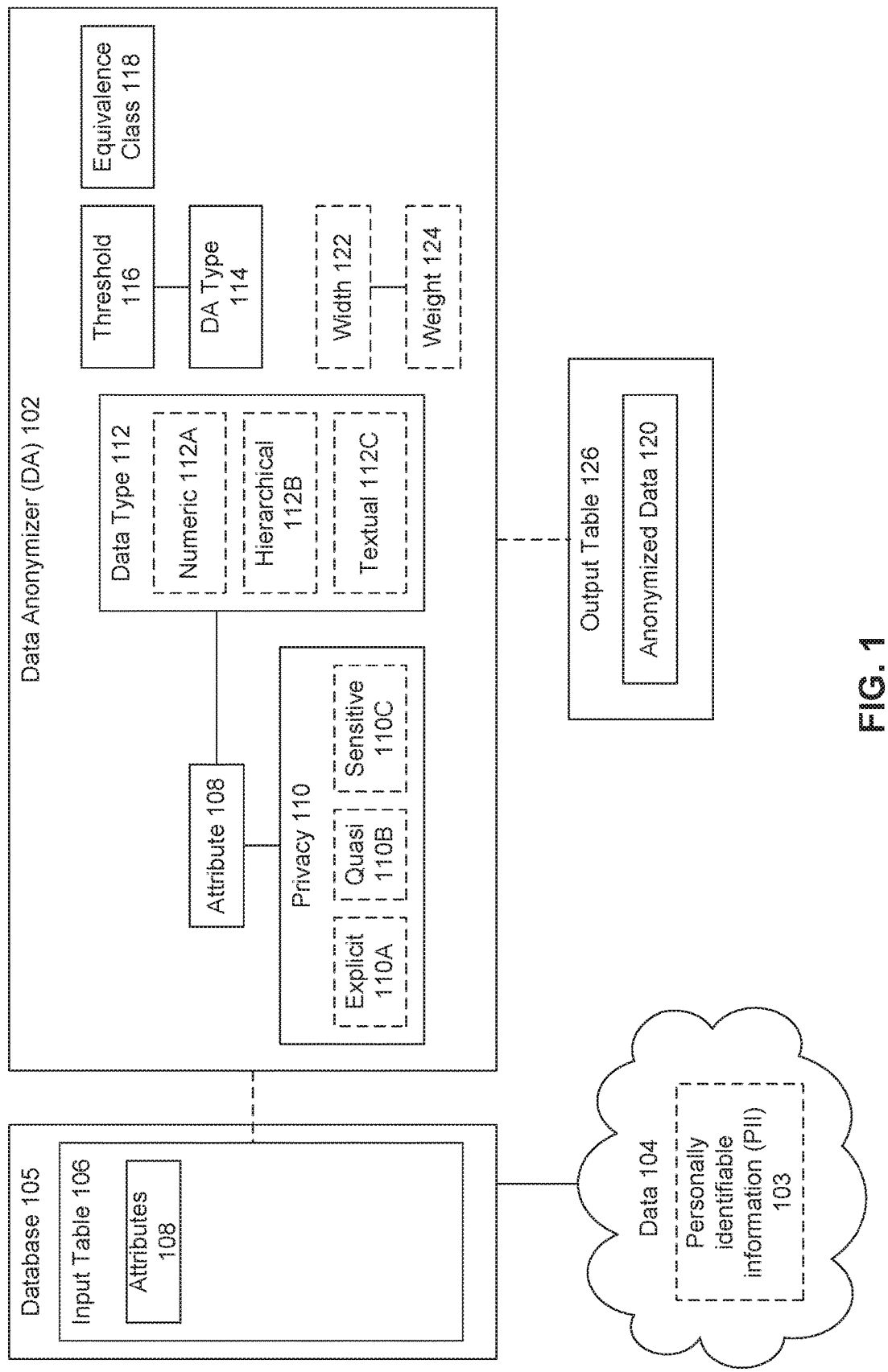
FIG. 1 is a block diagram illustrating example data anonymization functionality in an in-memory database, according to some embodiments.

FIG. 1 is a block diagram 100 illustrating example data anonymization functionality in an in-memory database, according to some embodiments. Data Anonymizer (DA) 102 may use data anonymization to protect the privacy or identity of individuals about whom data 104 has been collected and is being published or otherwise made publicly available.

In some embodiments, DA 102 may use various data anonymization techniques that delete, encrypt, or otherwise obscure personally identifiable information (PII) 103 within data 104 while maintaining as much of the remaining data as possible. PII 103 may include any data values, objects or types that may be used to identify or potentially identify particular individuals or companies about whom data 104 was collected. DA 102 may enable data 104 about individuals to be publicly released, while not releasing enough information to be able to identify the actual individuals about whom the data pertains.

For example, data 104 may have been collected from individuals for the purposes of medical or market research. The data 104 may include PII 103 that is useful for identifying the individuals and may have been used to test a hypothesis, conduct experiments, or perform studies. In an embodiment, the results of data analysis may be published in a journal or online, presented at a conference, or otherwise made publicly available. To support the results, portions of the data 104 used in the studies may be released as well. However, what is often unnecessary (and what may be desired to be avoided) is to release the specific identities of the individuals about whom the data 104 was collected.

DA 102 may anonymize portions of data 104 to remove or otherwise obscure PII 103 such that it is difficult or impossible to specifically identify an individual about whom the released anonymized data 120 pertains. With expanded anonymization techniques, as being applied to different data types 112, DA 102 may perform the minimum amount of anonymization necessary to protect the privacy of individuals while maintaining as much of the integrity of the remaining data 104 as possible.

Data 104 may be stored in a relational database or a non-relational database. DA 102 may receive data 104 from one or more sources and store the received data 104 across records of an input table 106. In an embodiment, input table 106 may include a table in a column-store or in-memory database 105. Organizing data 104 into a column-store, in-memory database 105 may enable DA 102 to perform various anonymization operations (e.g., such as sorting) very quickly relative to other storage mechanisms (such as disk storage in a relational database).

The data of input table 106 may be organized into a number of records, each record including a number of data values. The various records may correspond to one or more individuals or organizations about which data 104 was collected. Each record may include values which correspond to an attribute 108 that identifies what the particular values represent. Example attributes 108 may include name, social security number, salary, medical history, age, address, account balance, credit score, employer, education, relationship status, etc. <John Smith:43:New York> may be an example record with values for the attributes name, age, and location. As shown in the example of FIG. 1, input table 106 may include attributes 108, and DA 102 may receive or process a subset of those attributes 108 in the manner described herein.

In column-oriented database 105, attribute 108 may correspond to a row of input table 106 and may indicate what information is stored in the row, and each column may correspond to a particular record. In a row-oriented or relational database, the row and column designations may be reversed, such that each row corresponds to a record, and each column an attribute 108.

In an embodiment, different attributes 108 may be associated with different levels of privacy 110. Each privacy level 110 may indicate to what level of precision a particular individual can be identified or distinguished from one or more other individuals about whom PII 103 exists within data 104. Privacy 110 may be an indicator of how much or to what degree PII 103 exists within the values of the various attributes 108.

For example, explicit identifier information 110A may indicate that a particular value of an attribute 108 may be used to identify a specific individual or company or record from the data 104. In an embodiment, an explicit identifier 110A value may include a value distinguishable from other values for a particular attribute 108. Example explicit identifiers 110A may include name, social security number, and address.

In an embodiment, privacy 110 designations of particular attributes 108 may be designated relative to the values of other collected data 104. In different data sets 104, the privacy 110 of a particular attribute 108 may vary. For example, in a first data set with only one individual named "Mike Smith," the name attribute may be an explicit identifier 110A. However, in another data set in which data is only collected from individuals named "Mike Smith," the name attribute may not be an explicit identifier 110A, and may not be PII 103 at all.

A quasi-identifier 110B may indicate an attribute 108 whose value when considered together with one or more other attributes 108 (e.g., quasi-identifiers 110B) can potentially identify an individual record from data 104. Example quasi-identifiers 110B may include zip code, birthday, and gender. Any one of these values, when taken alone, may not be enough to distinguish or identify a particular individual or record from input table 106 relative to the other individuals. However, it is possible that (depending on the actual data values of the collected data 104) that any or particular combinations of the quasi attributes 110B may be used to identify an individual in the data set. For example, zip code and birthday may be enough to identify a specific individual in a particular data set. In an embodiment, a quasi-identifier 110B may need to be combined with one or more other quasi-identifiers 110B to identify or distinguish a particular individual or record.

A sensitive identifier 110C may include values (corresponding to an attribute 108) whose significance may be derived through attribution with a specific individual or record. Example sensitive attributes include age, health status, and salary. For example, knowing the identity of a specific an individual about whom particular salary information was collected may be sensitive information 110C. For example, knowing that Rachel Burns is earning $100,000/year may be sensitive information 110C. However, knowing that someone in a study is earning $100,000/year without knowing the identity to be Rachel Burn may not constitute sensitive information 110C.

In an embodiment, input table 106 may include the attributes: name, city, birthdate, and salary. DA 102 may receive an indication or designation (e.g., from a user or administrator who is familiar with values of data 104) as to which attributes 108 correspond to which privacy levels 110. For example, in a first data set, name may be explicit 110A, city and birthdate may be quasi 110B, and salary may be sensitive 110C. However, in a second data set with the same attributes 108 (but different values) the privacy designations 110 may be different.

In addition to being identified with a particular privacy level 110, attributes 108 may also be identified with a particular data type 112. Data type 112 may be an indication of what type of data values are stored in input table 106. Each attribute 108 may include its own data type 112. Three example data types 112 include numeric 112A, hierarchical 112B, and textual 112C. Numeric 112A may indicate that the values of attribute 108 are number values (integer, real, whole, decimal, currency, etc.). An example numeric data value may be salary.

In an embodiment, data type 112 may be applied to quasi attributes 110B as used by DA 102 to perform data anonymization functions. For example, data type 112 for quasi 110B may indicate how to partition the data during the data anonymization process. In an embodiment, different attributes 108 with number values (integer, real, whole, decimal, currency, etc.) may be defined as numerical 112A.

Hierarchical 112B may indicate that the data values adhere to a type of hierarchy, flow, or nesting. Example hierarchical data may include relative positions within a company organizational chart. For example, a company organizational chart may include the Chief Executive Officer (CEO) at the top with different positions flowing out from the root node of CEO that indicate a level of managerial hierarchy within the organization.

Textual 112C may indicate that the attribute 108 includes values that are to be interpreted as alpha-numeric strings or characters. In an embodiment, the textual 112C designation may be used on an attribute 108 that includes only numeric characters and is to be interpreted as textual 112C data rather than number 112A. An example of such data may be a string of numbers that correspond to a personal identifier or social security number. Other example textual data 112C may include name or address information. In an embodiment, address information may be broken down into both a numerical attribute 112A indicating building number, and a textual attribute 112C indicating the name of the road on which the building is located.

To perform data anonymization on the values of input table 106, DA 102 may receive an indication of a DA type 114 and a threshold value 116 from a user or data administrator corresponding to the different attributes 108. DA type 114 may indicate which particular data anonymization technique is to be applied to the values of data 104. In an embodiment, DA 102 may apply any combination of data anonymization techniques such as K-anonymity, L-diversity, and/or T-closeness, to name just some examples. Threshold value 116 may correspond to the selected or indicate the DA type 114, and indicate a level or degree of anonymization.

In some embodiments, in K-anonymity, the property K (i.e., threshold 116) may indicate that each record in anonymized data 120 must be indistinguishable from at least K-1 other records. Anonymized data 120 may include the published or output data after data anonymization, in which PII 103 has been reduced, grouped, removed, or otherwise obscured.

In an embodiment, DA 102 may apply K-anonymity with respect to the quasi-identifiers 110B. As is discussed in greater detail below, DA 102 may group records into various equivalence classes 118 based on a similarity or overlap of their quasi-identifier 110B values. Each equivalence class 118 may include at least K records (threshold 116) grouped based on various ranges for values as determined by DA 102.

In some embodiments, in L-diversity, the distribution of values for sensitive identifiers 110C within an equivalence class 118 must be at least L (i.e., threshold 116). For example, if salary is a sensitive identifier 110C, and L is 5, then in an equivalence class 118 for the anonymized or output data set 120, there must be at least 5 records sharing the same salary. In an embodiment, if there are fewer than the specified threshold 116 of records in an equivalence class 118, DA 102 may either suppress the records or combine the records with another equivalence class 118 to satisfy the threshold 116.

In some embodiments, T-closeness is a further refinement of L-diversity, in which the distribution of values for the sensitive identifier 110C within an equivalence class 118 is within T of the distribution of the sensitive identifier 110C for the entire data set.

Solely for purposes of illustration, and not limitation, the operations of DA 102 are described with respect to K-anonymity 114. In an embodiment, there may be two primary steps to performing the selected DA type 114 (e.g., K-anonymity) on the values of data 104 from input table 106. The first step may be determining or selecting which attribute(s) 108 to anonymize. The second step may be actually performing the data anonymization functionality on the actual values of the selected attribute(s) 108.

DA 102 may use the privacy 110 and data type 112 information to perform data anonymization on PII 103 using K-anonymity. For example, DA 102 may anonymize values corresponding to the indicated quasi-identifiers 110B to generate one or more equivalence classes 118 which are then output to output table 126. Output table 126 is used to store anonymized data 120.

In an embodiment, DA 102 may suppress explicit identifiers 110A and prevent their release into output table 126. In an embodiment, in K-anonymity, DA 102 may not anonymize sensitive identifiers 110C, but instead anonymize the quasi-identifiers 110B to prevent any association between the sensitive information 110C and the identity of an individual using PII 103.

DA 102 may generate one or more equivalence classes 118 as part of the data anonymization process. An equivalence class 118 may include a set of records within an anonymized data set 120 that have the same, similar, or overlapping values (or values that fall within a range) for one or more quasi identifiers 110B. For example, a group of records that share the same zip code, city, birthdate, and/or first name may belong to the same equivalence class 118. Other examples include identifiers that share one or more characters, or ages that fall within a range.

In an embodiment, DA 102 may calculate and use a width 122 of the various quasi-attributes 110B to determine or select which attribute(s) 108 to anonymize. Width 122 may be an indicator of how wide a range of values exist in data 104 for a particular attribute 108. In the case of K-anonymity, DA 102 may determine the width 122 for the various quasi-identifiers 110B and/or various combinations thereof.

In an embodiment, DA 102 may determine the relative widths 122 of the attributes 108 from the group of identified quasi-identifiers 110B. When data 104 is anonymized or abstracted, there may be a degree of information loss that occurs as part of the data anonymization process. In order to reduce the amount of information loss, DA 102 may select the attribute(s) 108 with the greatest width 122 or range of values for data anonymization. Selecting the attribute 108 with the greatest width 122 may reduce the amount of information loss that occurs during data anonymization. However, to accurately perform a width analysis across different attributes 108, DA 102 may need to account for the various different data types 112 corresponding to those attributes 108.

Normalized certainty penalty (NCP) measures information loss (e.g., width 122) or potential information loss for a single generated equivalence class 118 (partition) of data 104 pertaining to anonymizing a selected quasi-attribute 110B. In an embodiment, DA 102 may include different NCP calculation techniques based on the different data types 112 corresponding to the various attributes 108. DA 102 may calculate NCP for the various attributes 108 to determine which has the greatest width 122 or NCP. In an embodiment, the attribute 108 with the greatest width 122 or least information loss may be selected for anonymization by DA 102 (if threshold 116 is also satisfied by the anonymization of the selected attribute 108).

In an embodiment, NCP may be calculated and used to recursively split a data set into different partitions. For example, during a first iteration, an attribute 108 with a greatest NCP may be selected to be split. For example, if there are two quasi attributes age and workclass that have NCPs of 0.5 and 0.25, respectively, age may be selected to partition the data set during a first iteration. After the first iteration, the NCPs may be recalculated for the various quasi attributes, and if the threshold 116 has not been met, then the quasi attribute with the remaining highest NCP (which may be the same or different attribute) may be selected upon which to partition the data set during the second iteration. This process may be performed recursively until threshold 116 is satisfied.

In some embodiments, for numerical attributes 112A, the NCP (width 122) of an equivalence class 118 (partition P) on an attribute 108 may be defined as:

$$NCP_{A_{Num}}(P) = \frac{\max_{A_{num}}^P - \min_{A_{num}}^P}{\max_{A_{Num}} - \min_{A_{Num}}}$$

The numerator and denominator represent the ranges of the attribute $A_{num}$ for the partition P and the entire attribute domain, respectively. As used herein, in some embodiments, partition P and equivalence class 118 may be used interchangeably, wherein both may refer to a grouping of values from input table 106. For example, a partition may have an interval or actual data values ranging from 20 to 30 on attribute "Age." The partition may also include an interval or range of possible data values ranging from 20 to 60 in the entire attribute domain (of data 104). Then, for example, the NCP for the Age attribute may be calculated as (30–20)/(60–20)=0.25.

In some embodiments, for a hierarchical data type 112B, NCP (width 122) may be calculated as:

$$NCP_{A_{Cat}}(P) = \frac{\text{card}(u)}{A_{Cat}}$$

Figure 4:
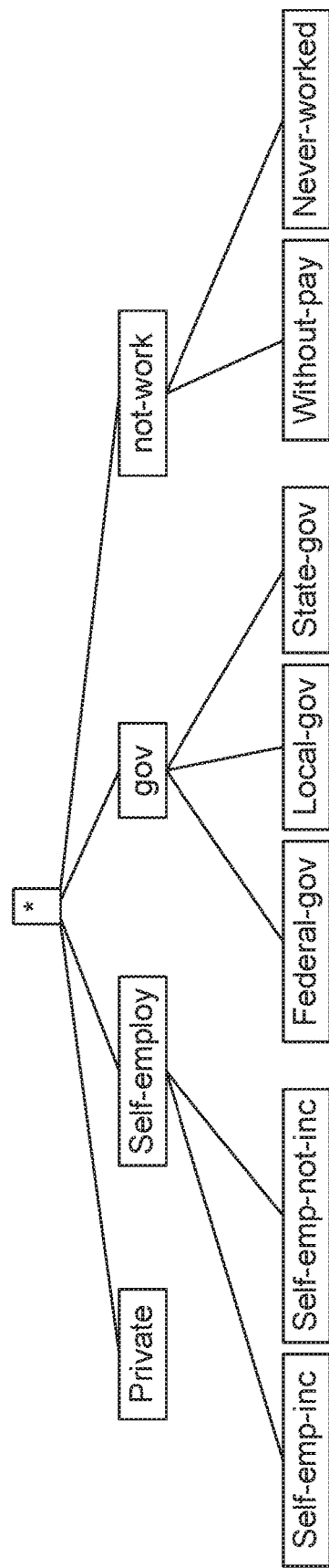
FIG. 4 is a block diagram illustrating example data anonymization functionality with respect to a hierarchical data type, according to an embodiment.

"u" may be the lowest common ancestor for $A_{cat}$ values included in P. "Card(u)" may be the number of leaves (i.e., attribute values) in the sub-tree of u, which may be the root node of the example partition shown in FIG. 4. FIG. 4 is a block diagram 400 illustrating example data anonymization functionality with respect to a hierarchical data type, according to an embodiment.

For example, in the hierarchy of attribute "Workclass" shown in FIG. 4, the root node * contains 8 leaves. If a partition's root is "self-employ," it contains 2 leaves. Thus, the normalized width (NCP) for the partition would be (2/8)=0.25.

In some embodiments, for a textual data type 112C, the NCP (width 122) may be calculated as:

$$NCP_{A_{Txt}}(P) = \frac{n_p \cdot \sum_{i=1}^{n_p} \text{Anonymized}(t_i)}{A_{txt} \cdot n_A}$$

The numerator and denominator represent the total number of anonymized characters of attribute $A_{num}$ for the partition P, and the total number of characters of attribute $A_{num}$ for data 104, respectively. $n_p$ is the number of records in the partition, and $n_a$ is the number of records of the entire dataset 104. Anonymized($t_i$) is the number of anonymized characters for tuple $t_i$. $A_{txt}$ is the total number of characters of attribute for $A_{num}$ for data 104.

Figure 5:
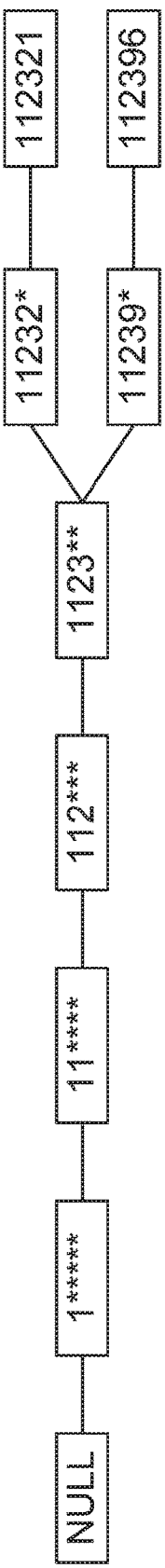
FIG. 5 is a block diagram illustrating example data anonymization functionality with respect to a textual data type, according to an embodiment.

A partition may contain two records with values "112321" and "112396" on attribute "Final_Weight" which is identified as textual 112C. While there may be no specified hierarchy or nesting for Final_Weight, DA 102 may create an example internal hierarchy as shown in FIG. 5. FIG. 5 is a block diagram 500 illustrating example data anonymization functionality with respect to a textual data type, according to an embodiment.

The hierarchy may be generated based on identification of a common string or root (if any). As shown in FIG. 5, the two values may be generalized to a common string, also known as a root, "1123". The number of anonymized characters for the root is 2 (as indicated by the ). The number of characters anonymized in the partition is 4. The total number of characters for the data set is 12 (6 in each value, though in other examples, the number of characters of different values may vary), and there are 2 records in the partition, and 8 total records in the database. The NCP may then be calculated as: 2*4/12*8=0.08.

In an embodiment, the width 122 may also be weighted. Weight 124 may indicate an importance or relative importance of the quasi identifiers 110B. The greater the weight, the more important the values of the attribute 108 may be to the research study or data integrity. In some embodiments, weighted NCP may be calculated as follows:

$$WNCP_{A_i}(P) = W_i * NCP_{A_i}(P)$$

In an embodiment, privacy 110, data type 112, and weight 124 may be provided to DA 102 in the form of extensible markup language (XML). In an example embodiment, in which the Age attribute has a weight of 100, the XML may indicate <quasi Attribute name="Age" type="number" weight=100/>.

As noted above, the attribute 108 (quasi-attribute 110B) with the highest weighted NCP may then be selected for partitioning (e.g., data anonymization). As used herein, in some embodiments, partitioning and data anonymization may be used interchangeably to refer to the processing performed by DA 102 that removes or obscures PII 103 from data 104, and is used to generate anonymized data 120.

In an embodiment, DA 102 may recursively perform partitioning or partition splitting based on data type 112, until the threshold 116 for the selected DA type 114 is satisfied. For example, DA 102 may recursively partition data 104 based on an attribute 108 with the greatest width 122 until each of the generated equivalence classes 118 includes at least K records (satisfying threshold 116) for K-anonymity (DA type 114).

In performing data anonymization or partitioning for numerical attributes 112A, a partition or data set of input table 106 may be split into two partitions (or data sets) based on the median value of an attribute 108. An example, numerical partitioning split algorithm is shown below.

```
splitNumerical(partition, dimension){
    median = find the median value on dimension for partition;
    for each tuple t_i in partition on dimension {
        if (t_i < median)
            store t_i to p_smaller;
        else
            store t_i to p_bigger;
        return p_smaller ∪ p_bigger
}
```

For hierarchical attributes 112B, DA 102 may create a hierarchical tree on the attribute 108 with one root and a number of sub-groups. DA 102 may ensure that each sub-group includes at least K records. If a particular sub-group does not include at least K records, then it is moved into an "Others" sub-group (which may not be one of the original sub-groups from input table 106).

As part of the partitioning process (for numerical data types 112A), any larger sub-groups that include more than 2K-1 records may be split into two sub-groups. At the end of the partitioning process, each remaining sub-group or equivalence class 118 may include at least K and no more than 2K-1 records. In an embodiment, any sub-groups with fewer than K records may either be suppressed (e.g., excluded from anonymized data 120) or combined with other equivalence classes 118.

For hierarchical data 112B or textual data 112C, the number of sub groups may be determined by the number of children for the current parent. In an embodiment, a partition with greater than K records could be partitioned into further sub-groups. Or, for example, any sub-groups or equivalence classes with fewer than K records may be combined into another group.

An example, hierarchical partition split algorithm is shown below.

```
splitHierarchical (partition, dimension){
    root = get partition root node on dimension;
    for each child r_i of root{
        for each tuple t_i of partition on dimension{
            if (r_i covers t_i) {
                stores t_i into p_i;
                remove t_i from partition;
            }
        }
        replace root with r_i for the p_i sub partition;
    }
    store the rest of tuples into p_other;
    set root to the partition root;
    set split allowable to false for sub partition p_other on dimension;
    merge p_i, which has tuples less then k, into p_others;
    return p_i ∪ p_ohters
}
```

In some embodiments, splitting or partitioning textual attributes 112C begins with identifying a common string (if any) for the tuples or records. The tuples are then grouped into sub-groups with a common string (root). For example, starting with an empty string, DA 102 may scan values to identify a common character amongst multiple values of the attribute 108. If a common character is identified, it is added to the common string (root) in each iteration. At the end, the partition or data set is split into sub-partitions or equivalence classes 118, each sub-partition having the same root. In an embodiment, in partitioning of textual values 112C, DA 102 may generate a text-based hierarchy. An example textual partitioning algorithm is shown below.

```
splitTextual(partition, dimension){
    root = get partition root node on dimension;
    count = root.size( ) + 1;
    while (partition.size( ) > 0) {
        newroot = substring(t_0, count);
        for each tuple t_i in partition on dimension {
            r_i = substring(t_i, count);
            if (newroot == r_i){
                store t_i to p_i;
                remove t_i from partition;
            }
        }
        replace root with newroot for partition p_i;
    }
    merge p_i, which has tuples less then k, into p_others;
    set root to the partition root;
    set split allowable to false for sub partition p_other on dimension;
    return p_i ∪ p_ohters;
}
```

Table 1 below is an example of data that may be stored in input table 106 and received or made available to DA 102. The example data includes 8 records and 5 attributes 108. The attributes 108 may include the following privacy 110 designations: ID-explicit and Salary-sensitive, and Age, WorkClass, and Final_Weight may be quasi attributes 110B.

In some embodiments, the selected DA type 114 may be K-anonymity, and the threshold K 116 may be 2. The quasi-attributes 110B may include the following data type 112 designations: Age-numerical, WorkClass-hierarchical, and Final_Weight-textual attribute 112C.

TABLE 1

(Input Table 106)

| ID | Age | WorkClass | Final_Weight | Salary |
|---|---|---|---|---|
| 1 | 39 | State-gov | 112316 | <=50k |
| 2 | 50 | Self-employ | 215682 | <=50k |
| 3 | 38 | Private | 215646 | <=50k |
| 4 | 52 | Self-employ | 215642 | >50k |
| 5 | 31 | Private | 215681 | >50k |
| 6 | 30 | State-gov | 112319 | >50k |
| 7 | 25 | Self-employ | 112396 | <=50k |
| 8 | 56 | Local-gov | 112321 | >50k |

An example anonymization of the values of Table 1 based on Age, with K=2, is shown below in Table 2. As may be seen in Table 2, there are 4 equivalence classes 118 of Age, each containing at least (K) 2 records. Tables 2-5 below illustrate example output tables 126 which may be produced as a result of data anonymization by DA 102.

TABLE 2

(Anonymized based on Age, K = 2), GCP = 21.77%

| ID | Age | WorkClass | Final_Weight | Salary |
|---|---|---|---|---|
| 6 | 25-30 | State-gov | 112319 | >50k |
| 7 | 25-30 | Self-employ | 112396 | <=50k |
| 3 | 31-38 | Private | 215646 | <=50k |
| 5 | 31-38 | Private | 215681 | >50k |
| 1 | 39-50 | State-gov | 112316 | <=50k |
| 2 | 39-50 | Self-employ | 215682 | <=50k |
| 4 | 52-56 | Self-employ | 215642 | >50k |
| 8 | 52-56 | Local-gov | 112321 | >50k |

The values of Table 1 K-anonymized based on Work-Class, with K=2, generates 3 equivalence classes as follows in Table 3.

TABLE 3

(Anonymized based on WorkClass, K = 2), GCP = 14.06%

| ID | Age | WorkClass | Final_Weight | Salary |
|---|---|---|---|---|
| 3 | 38 | Private | 215646 | <=50k |
| 5 | 31 | Private | 215681 | >50k |
| 2 | 50 | Self-employ | 215682 | <=50k |
| 4 | 52 | Self-employ | 215642 | >50k |
| 7 | 25 | Self-employ | 112396 | <=50k |
| 1 | 39 | Gov | 112316 | >50k |
| 6 | 30 | Gov | 112319 | >50k |
| 8 | 56 | Gov | 112321 | >50k |

The values of Table 1 K-anonymized based on Final_Weight, with K=2, generates 4 equivalence classes as shown in Table 4 below.

TABLE 4

(Anonymized based on Final_Weight, K = 2), GCP = 2.6%

| ID | Age | WorkClass | Final_Weight | Salary |
|---|---|---|---|---|
| 7 | 25 | Self-employ | 1123** | <=50k |
| 8 | 56 | Local-gov | 1123** | >50k |
| 1 | 39 | State-gov | 11231* | <=50k |
| 6 | 30 | State-gov | 11231* | >50k |
| 3 | 38 | Private | 21564* | <=50k |
| 4 | 52 | Self-employ | 21564* | >50k |
| 2 | 50 | Self-employ | 21568* | <=50k |
| 5 | 31 | Private | 21568* | >50k |

An example of the values of Table 1 K-anonymized based on a combination of quasi-attributes 110A is shown below in Table 5. In the example of Table 5, the quasi-attributes 110B Age, WorkClass, and Final_Weight are used to generate 4 equivalence classes 118. In another embodiment, DA 102 may generate or process different combinations of quasi-attributes 110B as well, such as Age and WorkClass, Age and Final_Weight, and/or WorkClass and Final_Weight.

TABLE 5

(Anonymized based on Age, WorkClass, and Final_Weight, K = 2), GCP = 21.18%

| ID | Age | WorkClass | Final_Weight | Salary |
|---|---|---|---|---|
| 1 | 39-56 | Gov | 1123** | <=50k |
| 8 | 39-56 | Gov | 1123** | >50k |
| 6 | 25-30 | * | 1123** | >50k |
| 7 | 25-30 | * | 1123** | <=50k |
| 3 | 31-38 | Private | 2156** | <=50k |
| 5 | 31-38 | Private | 2156** | >50k |
| 2 | 50-52 | Self-employ | 2156** | <=50k |
| 4 | 50-52 | Self-employ | 2156** | >50k |

As shown in the examples above, a global certainty penalty (GCP) may be calculated for each example partitioning of data 104 based on various (combinations of) quasi-attributes 110B. In some embodiments, GCP for a table (T) may be calculated as follows:

$$GCP(T) = \frac{\sum_{i=1}^{m} G_i \cdot NCP(P_i)}{d \cdot n}$$

"n" may denote the number of records in the original table. "d" may indicate the number of quasi-identifiers 110B. "m" may be the number of equivalence classes $G_i$ is the number of records in the equivalence class $P_i$. GCP may produce a result between 0 and 1, or 0% and 100% if represented as a percentage.

As may be seen from the example just described, the quasi-attribute 110B with the least information loss may be the textual attribute 112C, Final_Weight. For example, in anonymizing the data 104 of Table 1 based on K-anonymity with K=2, DA 102 may use the quasi-identifier Final_Weight and produce the anonymized data 120 in the output table 126 of Table 4 shown above. In an embodiment, a quasi-attribute 110B may not be a single attribute (e.g., row), but may actually be several user-indicated attributes which together form a quasi-attribute 110B. As such, DA 102 may perform data anonymization on several attributes 108 which comprise a quasi-attribute 110B, simultaneously, together, or in parallel. The examples of Tables 2-4 showing a singular attribute 108 as a quasi-attribute 110B are exemplary only.

As described herein, DA 102 may perform data anonymization across a plurality of nodes and in parallel. For example, the values of input table 106 may be initially partitioned or separated based on the various quasi-attributes 108 or data type 112. The partitions may then be distributed to different nodes for parallel processing, and may be performed with regards to each attribute 108 to perform the above-referenced calculations in determining how to anonymize the values of input table 016 with the least amount of information loss.

Figure 2:
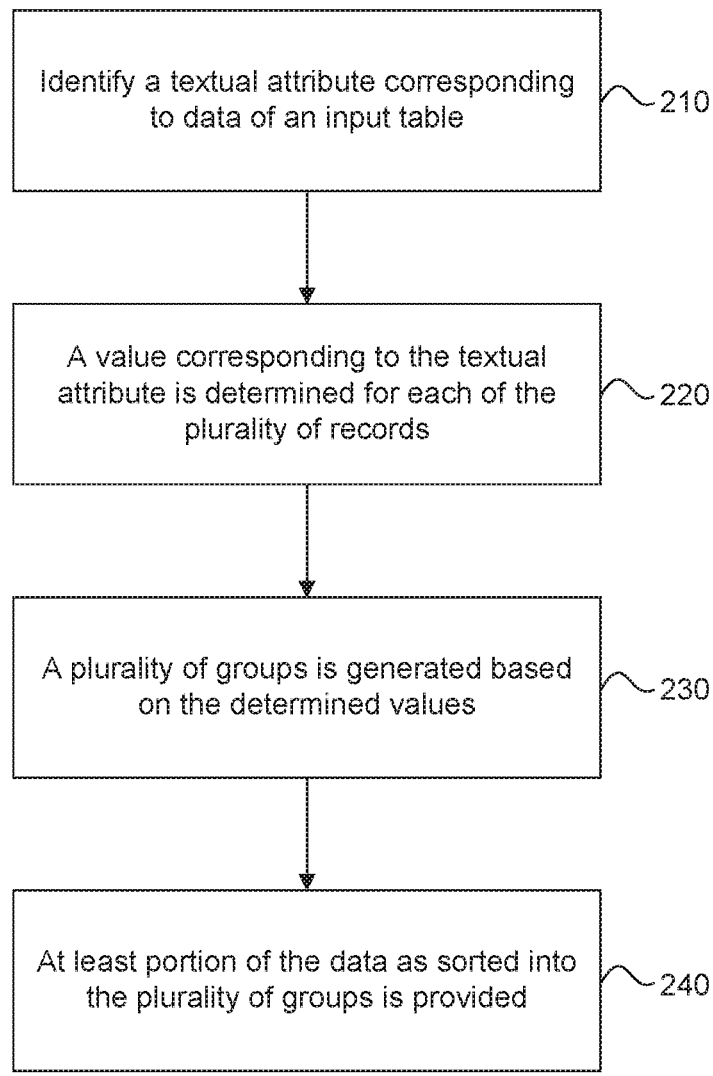
FIG. 2 is a flowchart illustrating a process for data anonymization, according to some embodiments.

FIG. 2 is a flowchart illustrating a process 200 for data anonymization, according to some embodiments. Method 200 can be performed by processing logic that can comprise hardware (e.g., circuitry, dedicated logic, programmable logic, microcode, etc.), software (e.g., instructions executing on a processing device), or a combination thereof. It is to be appreciated that not all steps may be needed to perform the disclosure provided herein. Further, some of the steps may be performed simultaneously, or in a different order than shown in FIG. 2, as will be understood by a person of ordinary skill in the art. Method 200 shall be described with reference to FIG. 1. However, method 200 is not limited to that example embodiment.

In 210, a textual attribute corresponding to data of an input table is identified. For example, in FIG. 1, DA 102 may determine that K-anonymity (DA type 114) is to be performed on data 104 as stored in input table 106. Based on the DA type 114, DA 102 may select the attributes 108 designated as quasi-identifiers 110B from input table 106. At least one of the quasi-identifier attributes 110B may be of a textual data type 112C. In an embodiment, a user or administer may provide DA type 114 to DA 102 via an XML file, and based on the XML file, DA 102 may determine the which quasi-attributes 110B are textual 112C.

The values stored in table 106 may be organized into records. The records may correspond to particular individuals about whom the data 104 has been collected, and may include PII 103. Based on the provided K-value (threshold 116), DA 102 may anonymize the selected quasi-identifier attribute 110B to protect the PII 103 from being published. Threshold 116 may indicate to what extent the data 104 is to be anonymized.

In 220, a value corresponding to the textual attribute for each of the plurality of records is determined. For example, input table 106 may include various values corresponding to the selected quasi-attribute 110B. The values may include alpha-numeric text, including one or more characters.

In 230, a plurality of groups are generated based on the determined values. For example, DA 102 may group the values of one or more selected quasi-attributes 110B into a number of equivalence classes 118 based on threshold 116. Example groupings are shown in Tables 2-5. As shown in Table 4, the values of each group may share one or more common characters.

In 240, at least portion of the data as sorted into the plurality of groups is provided. For example, the anonymized data 120 may be provided via output table 126 to the extent threshold 116 is satisfied. Any data groupings that do not satisfy threshold 116 may be suppressed or otherwise not provided in output table 126. As described in the example above, Table 4 with the lowest information loss may be selected and used as output table 126.

Figure 3:
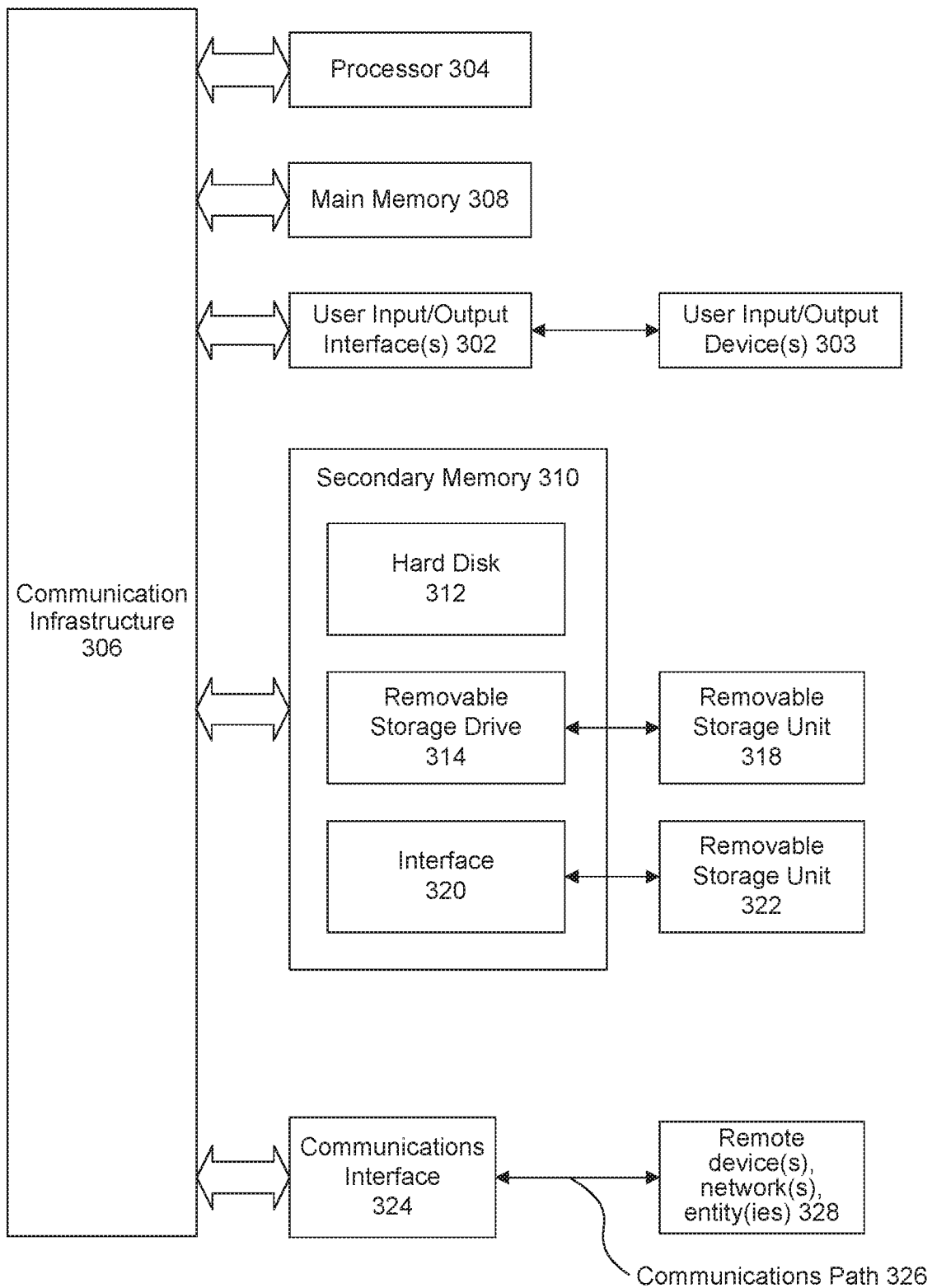
FIG. 3 is an example computer system useful for implementing various embodiments.

Various embodiments may be implemented, for example, using one or more well-known computer systems, such as computer system 300 shown in FIG. 3. One or more computer systems 300 may be used, for example, to implement any of the embodiments discussed herein, as well as combinations and sub-combinations thereof.

Computer system 300 may include one or more processors (also called central processing units, or CPUs), such as a processor 304. Processor 304 may be connected to a communication infrastructure or bus 306.

Computer system 300 may also include user input/output device(s) 303, such as monitors, keyboards, pointing devices, etc., which may communicate with communication infrastructure 306 through user input/output interface(s) 302.

One or more of processors 304 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 300 may also include a main or primary memory 308, such as random access memory (RAM). Main memory 308 may include one or more levels of cache. Main memory 308 may have stored therein control logic (i.e., computer software) and/or data.

Computer system 300 may also include one or more secondary storage devices or memory 310. Secondary memory 310 may include, for example, a hard disk drive 312 and/or a removable storage device or drive 314. Removable storage drive 314 may be a floppy disk drive, a magnetic tape drive, a compact disk drive, an optical storage device, tape backup device, and/or any other storage device/drive.

Removable storage drive 314 may interact with a removable storage unit 318. Removable storage unit 318 may include a computer usable or readable storage device having stored thereon computer software (control logic) and/or data. Removable storage unit 318 may be a floppy disk, magnetic tape, compact disk, DVD, optical storage disk, and/any other computer data storage device. Removable storage drive 314 may read from and/or write to removable storage unit 318.

Secondary memory 310 may include other means, devices, components, instrumentalities or other approaches for allowing computer programs and/or other instructions and/or data to be accessed by computer system 300. Such means, devices, components, instrumentalities or other approaches may include, for example, a removable storage unit 322 and an interface 320. Examples of the removable storage unit 322 and the interface 320 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 300 may further include a communication or network interface 324. Communication interface 324 may enable computer system 300 to communicate and interact with any combination of external devices, external networks, external entities, etc. (individually and collectively referenced by reference number 328). For example, communication interface 324 may allow computer system 300 to communicate with external or remote devices 328 over communications path 326, which may be wired and/or wireless (or a combination thereof), and which may include any combination of LANs, WANs, the Internet, etc. Control logic and/or data may be transmitted to and from computer system 300 via communication path 326.

Computer system 300 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 300 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 300 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 300, main memory 308, secondary memory 310, and removable storage units 318 and 322, as well as tangible articles of manufacture embodying any combination of the foregoing. Such control logic, when executed by one or more data processing devices (such as computer system 300), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 3. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A computer implemented method, comprising:
identifying a plurality of textual attributes, including both a first textual attribute and a second textual attribute, corresponding to personal identifying information stored across a plurality of records of an input table for anonymization based on at least a threshold for a number of values required in each of one or more groupings of the data;
determining a plurality of values for both the first and second textual attributes, wherein each value comprises one or more characters and corresponds to at least one of the plurality of records, and wherein a subset of the plurality of values comprises a plurality of unique values;

determining a width of both the first textual attribute and the second textual attribute based on the plurality of unique values, wherein the width corresponds to a range of the unique values associated with a respective attribute;

selecting the first textual attribute based on its width being greater than a width of the second textual attribute, wherein the greater width corresponds to a likelihood of reduced data loss through the anonymization;

generating a plurality of groups based on the determined plurality of values, wherein each group includes one or more of the determined plurality of values that share one or more common characters; and providing at least portion of the personal identifying information as sorted into the plurality of groups, wherein a count of the values of each group satisfies the threshold.

2. The method of claim 1, wherein the providing comprises:
determining that the count of values for a particular one of the plurality of groups is less than the threshold; and
suppressing the particular one of the plurality of groups that is less than the threshold, wherein the providing comprises providing the data sorted into the plurality of groups except for the particular group.

3. The method of claim 1, wherein the personal information of the data includes:
an explicit identifier attribute from which a particular record of the data is distinguishable from one or more remaining records of the data, wherein based on the explicit identifier, an individual corresponding to the record is identifiable;
a first quasi-identifier attribute which when considered together with a second quasi-identifier attribute identify the individual corresponding to the record; and
a sensitive data attribute which includes personal information corresponding to the individual.

4. The method of claim 3, wherein the textual attribute corresponds to the first quasi-identifier attribute.

5. The method of claim 1, wherein the identifying comprises identifying a numerical attribute and a hierarchical attribute in addition to the plurality of textual attributes.

6. The method of claim 1, wherein the selecting further comprises:
determining a weight corresponding to the first textual attribute;
determining a weight corresponding to the second textual attribute;
determining a weighted width for both the first textual attribute and the second textual attribute; and
selecting the first textual attribute based on its weighted width being greater than a width of the second textual attribute.

7. A system, comprising:
a memory; and
at least one processor coupled to the memory and configured to:
identify a plurality of textual attributes, including both a first textual attribute and a second textual attribute, corresponding to personal identifying information stored across a plurality of records of an input table for anonymization based on at least a threshold for a number of values required in each of one or more groupings of the data;
determine a plurality of values for both the first and second textual attributes, wherein each value comprises one or more characters and corresponds to at least one of the plurality of records, and wherein a subset of the plurality of values comprises a plurality of unique values;
determine a width of both the first textual attribute and the second textual attribute based on the plurality of unique values, wherein the width corresponds to a range of the unique values associated with a respective attribute;
select the first textual attribute based on its width being greater than a width of the second textual attribute, wherein the greater width corresponds to a likelihood of reduced data loss through the anonymization;
generate a plurality of groups based on the determined plurality of values, wherein each group includes one or more of the determined plurality of values that share one or more common characters; and
provide at least portion of the personal identifying information as sorted into the plurality of groups, wherein a count of the values of each group satisfies the threshold.

8. The system of claim 7, wherein the processor that provides is configured to:
determine that the count of values for a particular one of the plurality of groups is less than the threshold; and
suppress the particular one of the plurality of groups that is less than the threshold, wherein the providing comprises providing the data sorted into the plurality of groups except for the particular group.

9. The system of claim 7, wherein the personal information of the data includes:
an explicit identifier attribute from which a particular record of the data is distinguishable from one or more remaining records of the data, and wherein based on the explicit identifier, an individual corresponding to the record is identifiable;
a first quasi-identifier attribute which when considered together with a second quasi-identifier attribute identify the individual corresponding to the record; and
a sensitive data attribute which includes personal information corresponding to the individual.

10. The system of claim 9, wherein the textual attribute corresponds to the first quasi-identifier attribute.

11. The system of claim 7, wherein the processor that identifies is configured to:
identify a numerical attribute and a hierarchical attribute in addition to the plurality of textual attributes.

12. The system of claim 7, wherein the processor that selects is further configured to:
determine a weight corresponding to the first textual attribute;
determine a weight corresponding to the second textual attribute;
determine a weighted width for both the first textual attribute and the second textual attribute; and
select the first textual attribute based on its weighted width being greater than a width of the second textual attribute.

13. A non-transitory computer-readable device having instructions stored thereon that, when executed by at least one computing device, causes the at least one computing device to perform operations comprising:
identifying a plurality of textual attributes, including both a first textual attribute and a second textual attribute, corresponding to personal identifying information stored across a plurality of records of an input table for anonymization based on at least a threshold for a number of values required in each of one or more groupings of the data;

determining a plurality of values for both the first and second textual attributes, wherein each value comprises one or more characters and corresponds to at least one of the plurality of records, and wherein a subset of the plurality of values comprises a plurality of unique values;

determining a width of both the first textual attribute and the second textual attribute based on the plurality of unique values, wherein the width corresponds to a range of the unique values associated with a respective attribute;

selecting the first textual attribute based on its width being greater than a width of the second textual attribute, wherein the greater width corresponds to a likelihood of reduced data loss through the anonymization;

generating a plurality of groups based on the determined plurality of values, wherein each group includes one or more of the determined plurality of values that share one or more common characters; and providing at least portion of the personal identifying information as sorted into the plurality of groups, wherein a count of the values of each group satisfies the threshold.

14. The non-transitory computer-readable device of claim 13, wherein the providing comprises:

determining that the count of values for a particular one of the plurality of groups is less than the threshold; and suppressing the particular one of the plurality of groups that is less than the threshold, wherein the providing comprises providing the data sorted into the plurality of groups except for the particular group.

15. The non-transitory computer-readable device of claim 13, wherein the personal information of the data includes:

an explicit identifier attribute from which a particular record of the data is distinguishable from one or more remaining records of the data, and wherein based on the explicit identifier, an individual corresponding to the record is identifiable;

a first quasi-identifier attribute which when considered together with a second quasi-identifier attribute identify the individual corresponding to the record; and a sensitive data attribute which includes personal information corresponding to the individual.

16. The non-transitory computer-readable device of claim 15, wherein the textual attribute corresponds to the first quasi-identifier attribute.

17. The non-transitory computer-readable device of claim 13, wherein the identifying comprises:

identifying a numerical attribute and a hierarchical attribute in addition to the plurality of textual attributes.

18. The method of claim 1, further comprising:

calculating a normalized certainty penalty corresponding to the information loss based on two or more different data types.

* * * * *